United States Patent
Glock

(10) Patent No.: US 7,071,146 B1
(45) Date of Patent: Jul. 4, 2006

(54) HERBICIDAL COMPOSITION

(75) Inventor: Jutta Glock, Mumpf (CH)

(73) Assignee: Syngenta Crop Protection, Inc., Greensboro, NC (US)

(*) Notice: Subject to any disclaimer, the term of this patent is extended or adjusted under 35 U.S.C. 154(b) by 734 days.

(21) Appl. No.: 09/068,877

(22) PCT Filed: Nov. 11, 1996

(86) PCT No.: PCT/EP96/04914

§ 371 (c)(1),
(2), (4) Date: May 21, 1998

(87) PCT Pub. No.: WO97/18712

PCT Pub. Date: May 29, 1997

(30) Foreign Application Priority Data

Nov. 11, 1996 (CH) .................. 3314/95

(51) Int. Cl.
*A01N 25/32* (2006.01)
*A01N 43/42* (2006.01)
*A01N 47/36* (2006.01)
*A01P 13/02* (2006.01)

(52) U.S. Cl. ................ 504/105; 504/243
(58) Field of Classification Search ........ 504/103, 504/105, 243
See application file for complete search history.

(56) References Cited

U.S. PATENT DOCUMENTS

| | | | |
|---|---|---|---|
| 5,009,699 A | 4/1991 | Brady et al. | 71/92 |
| 5,371,060 A | 12/1994 | Glock et al. | 504/106 |
| 5,380,852 A | 1/1995 | Schutze et al. | 546/174 |
| 5,393,734 A * | 2/1995 | Andrea et al. | 504/215 |
| 5,488,027 A | 1/1996 | Bauer et al. | 504/105 |
| 5,529,974 A | 6/1996 | Kerber | 504/112 |
| 5,532,203 A | 7/1996 | Fory et al. | 504/105 |
| 5,534,482 A * | 7/1996 | Ishida et al. | 504/215 |
| 5,541,148 A * | 7/1996 | Glock et al. | 504/112 |
| 5,599,996 A * | 2/1997 | Condon et al. | 564/442 |
| 6,124,240 A * | 9/2000 | Bieringer et al. | 504/105 |

FOREIGN PATENT DOCUMENTS

| | | |
|---|---|---|
| AU | 67002/86 | 7/1987 |
| DE | 36 00 288 | 7/1987 |
| DE | 41 23 469 | 1/1993 |
| DE | 43 15 153 | 11/1994 |
| DE | 43 23 122 | 1/1995 |
| EP | 0 304 409 | 2/1989 |
| EP | 0 477 808 | 4/1992 |
| EP | 0 492 366 | 7/1992 |
| EP | 0 492 367 | 7/1992 |
| EP | 0 502 740 | 9/1992 |
| EP | 0 558 448 | 9/1993 |
| EP | 0 597 807 | 5/1994 |
| EP | 0 600 836 | 6/1994 |
| EP | 0 679 646 | 11/1995 |
| WO | 91/07874 | 6/1991 |
| WO | 94/00987 | 1/1994 |
| WO | 94/26716 | 11/1994 |

OTHER PUBLICATIONS

Devine et al. "Herbicide Interactions with Herbicides, Synergists, and Safeners: Section 17.4, Safeners for Herbicides". in Physiology of Herbicide Action. PTR Prentice Hall: NJ. p. 276-387, 1993.*

Derwent Abstract 95-044560/07 (of DE 43 23 122) Jul. 10, 1993.

Derwent Abstract 93-027968/04 (of DE 41 23 469) Jul. 16, 1991.

* cited by examiner

Primary Examiner—S. Mark Clardy
(74) Attorney, Agent, or Firm—Thomas Hamilton

(57) ABSTRACT

A selectively herbicidal composition which comprises, besides customary inert formulation auxiliaries, as active ingredient a mixture of: a) a herbicidally active amount of a herbicide selected from the group consisting of the compounds of formula (Ia), and/or (Ib), in which R is hydrogen or fluorine and/or (Ic) or of a salt of the compounds of formulae (Ia) and/or (Ib) and/or (Ic), and b) a herbicidally antagonistically active amount of a compound of formula (IIa), of a compound of formula ($IIb_1$), of a compound of formula ($IIb_2$), of a compound of formula (IIc), of a compound of formula (IIe), of a compound of formula (IIf), or of a compound of formula (IIg), in which the substituents have the meanings given in claim 1.

13 Claims, No Drawings

HERBICIDAL COMPOSITION

This application is a 371 of International Application No. PCT/EP96/04914, filed Nov. 11, 1996 which is fully incorporated by reference herein.

The present invention relates to novel selectively herbicidal compositions for controlling grasses and weeds in crops of useful plants, in particular in cereal and rice crops, which comprise a herbicide and a safener (antidote) and which protect the useful plants, but not the weeds, against the phytotoxic activity of the herbicide, and to the use of this composition for controlling weeds in crops of useful plants.

When using herbicides, it is possible that the crop plants are also damaged to a considerable extent, for example depending on the herbicide dose and the type of application, the crop plant, the soil constitution and the climatic factors such as photoperiod, temperature and precipitation amounts.

To deal with this and similar problems, a variety of substances have already been proposed as safeners which are capable of antagonizng the damaging effect of the herbicide on the crop plant, ie. of protecting the crop plants from it, while the herbicidal activity on the weeds to be controlled is virtually not adversely affected. It has emerged that the safeners proposed frequently act in a highly specific manner, both with a view to the crop plants and with a view to the herbicide and, in some cases, also as a function of the type of application, which means that a particular safener is frequently only suitable for a particular crop plant and a specific class of herbicidal substance, or a particular herbicide.

It has now been found that safeners disclosed in EP-A-492 366, WO 91/7874 and WO 94/987 are suitable for protecting crop plants against the phytotoxic action of sulfonylurea and sulfamoylurea herbicides which are described in EP-A-679 646, EP-A-502 740, EP-A-0 477 808 and U.S. Pat. No. 5,009,699.

According to the invention, there is thus proposed a selectively herbicidal composition which comprises, besides customary inert formulation auxiliaries such as carriers, solvents and wetting agents, as active ingredient a mixture of a) a herbicidally active amount of a herbicide selected from the group consisting of the compounds of the formula Ia

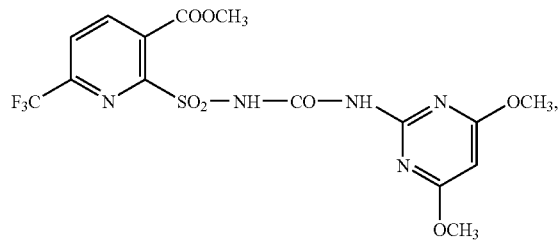

and/or Ib

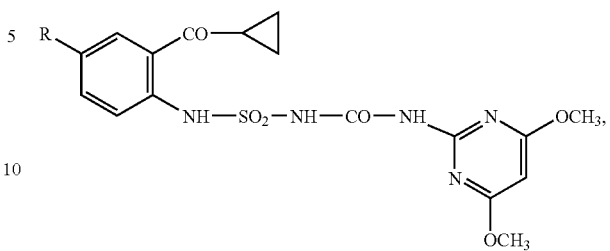

in which R is hydrogen or fluorine
and/or Ic

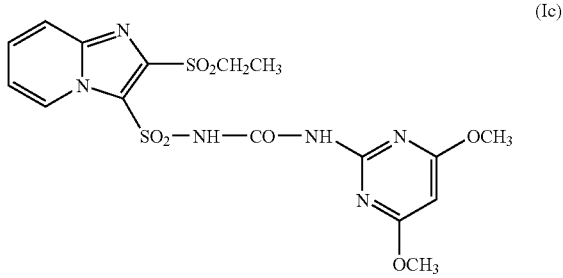

or of a salt of the compounds of the formulae Ia and/or Ib and/or Ic and b) a herbicidally antagonistically active amount of a compound of the formula IIa

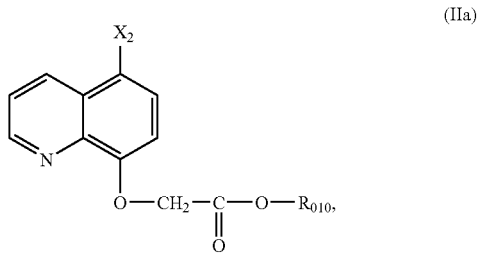

in which $R_{010}$ is hydrogen, $C_1$–$C_8$alkyl or $C_1$–$C_8$alkyl which is substituted by $C_1$–$C_6$alkoxy or $C_3$–$C_6$alkenyloxy and $X_2$ is hydrogen or chlorine, of a compound of the formula $IIb_1$

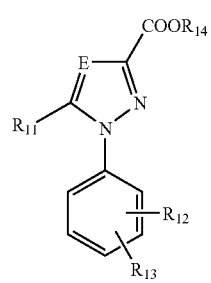

in which

E is nitrogen or methine $R_{11}$ is —CCl$_3$ or phenyl which is unsubstituted or substituted by halogen, $R_{12}$ and $R_{13}$ independently of one another are hydrogen or halogen, and $R_{14}$ is $C_1$–$C_4$alkyl, of a compound of the formula II$_2$

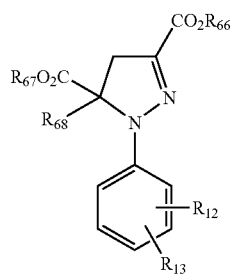

(IIb2)

in which $R_{12}$ and $R_{13}$ have the abovementioned meanings and $R_{66}$, $R_{67}$ and $R_{68}$ independently of one another are $C_1$–$C_4$alkyl, of a compound of the formula IIc

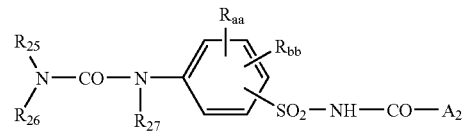

(IIc)

in which $A_2$ is a group

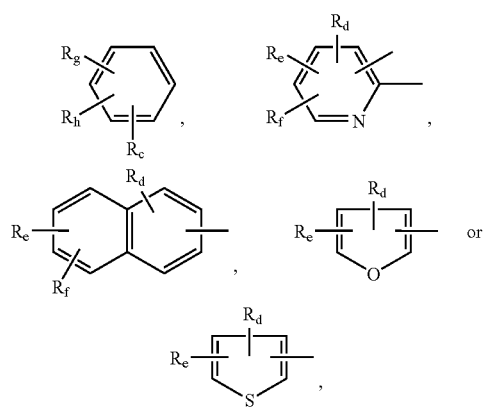

$R_{25}$ and $R_{26}$ independently of one another are hydrogen, $C_1$–$C_8$alkyl, $C_3$–$C_8$cycloalkyl, $C_3$–$C_6$alkenyl, $C_3$–$C_6$alkynyl,

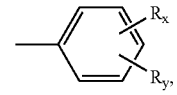

or $C_1$–$C_4$alkyl which is substituted by $C_1$–$C_4$alkoxy or or $R_{25}$ and $R_{26}$ together form a $C_4$–$C_6$alkylene bridge which can be interrupted by oxygen, sulfur, SO, SO$_2$, NH or —N($C_1$–$C_4$alkyl)-, $R_{27}$ is hydrogen or $C_1$–$C_4$alkyl;

$R_{aa}$ is hydrogen, halogen, cyano, trifluoromethyl, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —COOR$_j$, —CONR$_k$R$_m$, —COR$_n$, —SO$_2$NR$_k$R$_m$ or —OSO$_2$—$C_1$–$C_4$alkyl;

$R_g$ is hydrogen, halogen, cyano, nitro, $C_1$–$C_4$alkyl, $C_1$–$C_4$haloalkyl, $C_1$–$C_4$alkylthio, $C_1$–$C_4$alkylsulfinyl, $C_1$–$C_4$alkylsulfonyl, —COOR$_j$, —CONR$_k$R$_m$, —COR$_n$, —SO$_2$NR$_k$R$_m$, —OSO$_2$—$C_1$–$C_4$alkyl, $C_1$–$C_6$alkoxy or $C_1$–$C_6$alkoxy which is substituted by $C_1$–$C_4$alkoxy or halogen, $C_3$–$C_6$alkenyloxy or $C_3$–$C_6$alkenyloxy which is substituted by halogen, or $C_3$–$C_6$-alkynyloxy, or $R_{aa}$ and $R_{bb}$ together form a $C_3$–$C_4$alkylene bridge which can be substituted by halogen or $C_1$–$C_4$alkyl, or form a $C_3$–$C_4$alkylene bridge which can be substituted by halogen or $C_1$–$C_4$-alkyl, or form a $C_4$-alkadienylene bridge which can be substituted by halogen or $C_1$–$C_4$-alkyl;

$R_{bb}$ and $R_h$ independently of one another are hydrogen, halogen, $C_1$–$C_4$alkyl, trifluoromethyl, $C_1$–$C_6$alkoxy, $C_1$–$C_6$alkylthio or —COOR$_j$;

$R_c$ is hydrogen, halogen, nitro, $C_1$–$C_4$alkyl or methoxy; $R_d$ is hydrogen, halogen, nitro, $C_1$–$C_4$alkyl, $C_1$–$C_4$alkoxy, $C_1$–$C_4$alkylthio, $C_1$–$C_4$alkylsulfinyl, $C_1$–$C_4$alkylsulfonyl, —COOR$_j$ or —CONR$_k$R$_m$;

$R_e$ is hydrogen, halogen, $C_1$–$C_4$alkyl, —COOR$_j$, trifluoromethyl or methoxy, or $R_d$ and $R_e$ together form a $C_3$–$C_4$alkylene bridge;

$R_f$ is hydrogen, halogen or $C_1$–$C_4$alkyl;

$R_x$ and $R_y$ independently of one another are hydrogen, halogen, $C_1$–$C_4$alkyl, $C_1$–$C_4$alkoxy, $C_1$–$C_4$alkylthio, —COOR$_{28}$, trifluoromethyl, nitro or cyano;

$R_j$, $R_k$ and $R_m$ independently of one another are hydrogen or $C_1$–$C_4$alkyl; or $R_k$ and $R_m$ together form a $C_4$–$C_6$alkylene bridge which can be interrupted by oxygen, NH or —N($C_1$–$C_4$alkyl)-;

$R_n$ is $C_1$–$C_4$alkyl, phenyl, or phenyl which is substituted by halogen, $C_1$–$C_4$alkyl, methoxy, nitro or trifluoromethyl;

$R_{28}$ is hydrogen, $C_1$–$C_{10}$alkyl, $C_1$–$C_4$alkoxy-$C_1$–$C_4$alkyl, $C_1$–$C_4$alkylthio-$C_1$–$C_4$alkyl, di-$C_1$–$C_4$alkylamino-$C_1$–$C_4$alkyl, halo-$C_1$–$C_8$alkyl, $C_2$–$C_8$alkenyl, halo-$C_2$–$C_8$alkenyl, $C_3$–$C_8$alkynyl, $C_3$–$C_7$Cycloalkyl, halo- $C_3$–$C_7$-cycloalkyl, $C_1$–$C_8$alkylcarbonyl, allylcarbonyl, $C_3$–$C_7$cycloalkylcarbonyl, benzoyl which is unsubstituted or up to trisubstituted on the phenyl ring by identical or different substituents from the series consisting of halogen, $C_1$–$C_4$alkyl, halo-$C_1$–$C_4$-alkyl, halo-$C_1$–$C_4$alkoxy or $C_1$–$C_4$alkoxy; or furoyl, thienyl; or $C_1$–$C_4$alkyl which is substituted by phenyl, halophenyl, $C_1$–$C_4$alkylphenyl, $C_1$–$C_4$alkoxyphenyl, halo-$C_1$–$C_4$alkylphenyl, halo-$C_1$–$C_4$alkoxyphenyl, $C_1$–$C_6$alkoxycarbonyl, $C_1$–$C_4$alkoxy-$C_1$–$C_8$alkoxycarbonyl, $C_3$–$C_8$alkenyloxycarbonyl, $C_3$–$C_8$alkynyloxycarbonyl, $C_1$–$C_8$-alkylthiocarbonyl, $C_3$–$C_8$alkenylthiocarbonyl, $C_3$–$C_8$alkynylthiocarbonyl, carbamoyl, mono-$C_1$–$C_4$alkylaminocarbonyl, di-$C_1$–$C_4$alkylaminocarbonyl; or phenylaminocarbonyl, which is unsubstituted or up to trisubstituted on the phenyl by identical or different substituents from the series consisting of halogen, $C_1$–$C_4$alkyl, halo-$C_1$–$C_4$alkyl, halo-$C_1$–$C_4$alkoxy or $C_1$–$C_4$alkoxy or monosubstituted by cyano or nitro, or dioxolan-2-yl which is unsubstituted or substituted by one or two $C_1$–$C_4$alkyl radicals, or dioxan-2-yl which is unsubstituted or substituted by one or two $C_1$–$C_4$alkyl radicals, or $C_1$–$C_4$alkyl which is substituted by cyano, nitro, carboxyl or $C_1$–$C_8$alkylthio-$C_1$–$C_8$alkoxycarbonyl, of a compound of the formula IIe

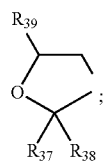
(IIe)

in which $R_{33}$ and $R_{34}$ independently of one another are $C_1$–$C_6$alkyl or $C_2$–$C_6$alkenyl; or $R_{33}$ and $R_{34}$ together are

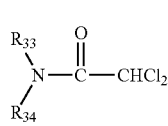

$R_{35}$, and $R_{36}$ independently of one another are hydrogen or $C_1$–$C_6$alkyl;

or $R_{33}$ and $R_{34}$ together are

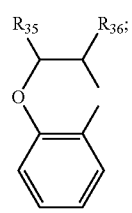

$R_{37}$ and $R_{38}$ independently of one another are $C_1$–$C_4$alkyl, or $R_{37}$ and $R_{38}$ together are —(CH$_2$)$_5$—;

$R_{39}$ is hydrogen, $C_1$–$C_4$alkyl or

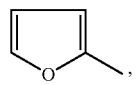

or $R_{33}$ and $R_{34}$ together are

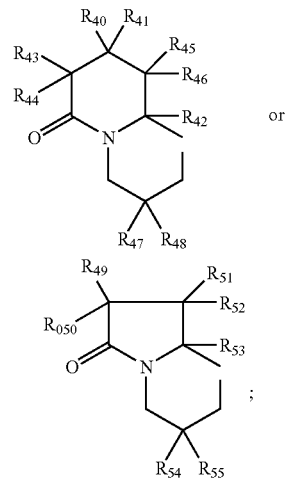

$R_{40}$, $R_{41}$, $R_{42}$, $R_{43}$, $R_{44}$, $R_{45}$, $R_{46}$, $R_{47}$, $R_{48}$, $R_{49}$, $R_{050}$, $R_{51}$, $R_{52}$, $R_{53}$, $R_{54}$ and $R_{55}$ independently of one another are hydrogen or $C_1$–$C_4$alkyl;

of a compound of the formula IIf

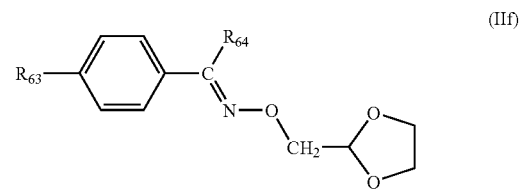
(IIf)

in which $R_{63}$ is hydrogen or chlorine and $R_{64}$ is cyano or trifluoromethyl, or of a compound of the formula IIg

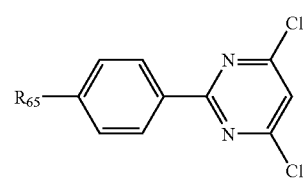
(IIg)

in which $R_{65}$ is hydrogen or methyl.

The invention also embraces the agronomically tolerated salts which the compounds of the formulae Ia, Ib and Ic can form, for example with amines, alkali metal bases and alkaline earth metal bases or quaternary ammonium bases.

Preferred salt formers amongst the alkali metal hydroxides and alkaline earth metal hydroxides are the hydroxides of lithium, sodium, potassium, magnesium or calcium, but in particular those of sodium or potassium.

Examples of amines which are suitable for ammonium salt formation are not only ammonia, but also primary, secondary and tertiary $C_1$–$C_{18}$alkylamines, $C_1$–$C_4$hydroxyalkylamines and $C_2$–$C_4$alkoxyalkylamines for example methylamine, ethylamine, n-propylamine, iso-propylamine, the four isomeric butylamine, n-amylamine, iso-amylamine, hexylamine, heptylamine, octylamine, nonylamine, decylamine, pentadecylamine, hexadecylamine, heptadecylamine, octadecylamine, methylethylamine, methyl-iso-propylamine, methylhexylamine, methylnonylamine, methylpentadecylamine, methyloctadecylamine, ethylbutylamine, ethylheptylamine, ethyloctylamine, hexylheptylamine, hexyloctylamine, dim-ethylamine, diethylamine, di-n-propylamine, di-iso-propylamine, di-n-butylamine, di-n-amylamine, di-iso-amylamine, dihexylamine, diheptylamine, dioctylamine, ethanolamine, n-propanolamine, iso-propanolamine, N,N-diethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine, propylenediamine, trimethylamine, triethylamine, tri-n-propylamine, tri-iso-propylamine, tri-n-butylamine, tri-isobutylamine, tri-sec-butylamine, tri-n-amylamine, methoxyethylamine and ethoxyethylamine; heterocyclic amines, for example pyridine, quinoline, iso-quinoline, morpholine, piperidine, pyrrolidine, indoline, quinuclidine and azepine; primary arylamines, for example anilines, methoxyanilines, ethoxyanilines, o,m,p-toluidines, phenylenediamines, benzidines, naphthylamines and o,m,p-chloroanilines; but in particular triethylamine, iso-propylamine and di-iso-propylamine.

The alkyl groups in the definitions of substituents in the compounds of the formulae IIa to IIg can be straight-chain or branched and are, for example, methyl, ethyl, n-propyl, iso-propyl, n-butyl, sec-butyl, iso-butyl, tert-butyl and pentyl, hexyl, heptyl, octyl, nonyl, decyl and their branched isomers. These alkyl groups can carry further substituents, for example halogen, in particular fluorine, chlorine or bromine, alkoxy, thioalkyl, cycloalkyl, phenyl, amino, acyl (for example $R_8CO$—) or oxo (O═). Suitable alkoxy, thioalkyl, haloalkyl and haloalkoxy groups are derived from the alkyl groups mentioned.

Examples of unsaturated groups of substituents are ethenyl, propenyl, butenyl, pentenyl, hexenyl, heptenyl, octenyl, ethynyl, propynyl, butynyl, pentynyl, hexynyl, heptynyl, octynyl and isomers which differ by the different position of the unsaturated bond, or bonds, in the molecule, isomers which contain branchings, and, in the case of the alkenes, cis and trans isomers.

Examples of alkenyloxy, alkynyloxy, haloalkenyl and haloalkenyloxy groups can be derived from the alkyl groups mentioned.

Cycloalkyl groups embrace, for example cyclopropyl, cyclobutyl, cyclopentyl, cyclohexyl, cycloheptyl and cyclooctyl. Corresponding cycloalkenes can be mono- or polyunsaturated.

The term "substituted" suggests not only monosubstitution, but also polysubstitution, if this is possible in the group in question.

Amongst the salts of the compound of the formula Ia, the compound of the formula Id

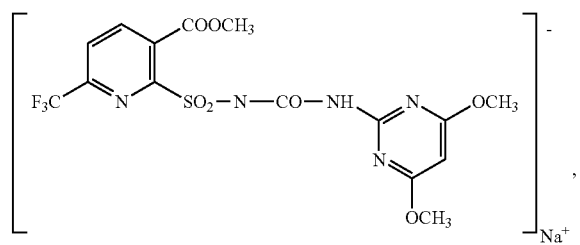

is particularly suitable for the composition according to the invention.

An especially preferred composition according to the invention comprises, as herbicide, either the compound of the formula Ia or Id and, as safener, the compound of the formula IIa in which $X_2$ is chlorine and $R_{010}$ is 1-methylhexyl.

Preferred compositions according to the present invention comprise, as safener, a compound of the formula IIa, IIb$_1$, IIb$_2$ or IIc.

Preferred compositions amongst those are compositions which comprise, as safener, a compound of the formula IIb$_1$ or IIb$_2$.

Another group of preferred compositions comprises, as safener, a compound of the formula IIa, and in particular such a compound of the formula IIa, in which $X_2$ is chlorine and $R_{010}$ is —CH(CH$_3$)C$_5$H$_{11}$-n.

Safeners which are especially suitable for use in the compositions according to the invention are listed in the tables which follow.

TABLE 1

Compounds of the formula IIa:

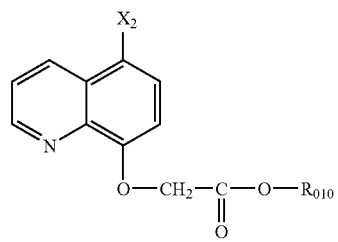

| Comp. No. | $X_2$ | $R_{010}$ |
|---|---|---|
| 4.01 | Cl | —CH(CH$_3$)—C$_5$H$_{11}$-n |
| 4.02 | Cl | —CH(CH$_3$)—CH$_2$OCH$_2$CH═CH$_2$ |
| 4.03 | Cl | H |
| 4.04 | Cl | C$_4$H$_9$-n |

TABLE 2

Compounds of the formula IIb$_1$

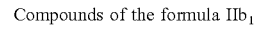

(IIb$_1$)

| Comp. No. | R$_{14}$ | R$_{11}$ | R$_{12}$ | R$_{13}$ | E |
|---|---|---|---|---|---|
| 5.01 | CH$_3$ | phenyl | 2-Cl | H | CH |
| 5.02 | CH$_3$ | phenyl | 2-Cl | 4-Cl | CH |
| 5.03 | CH$_3$ | phenyl | 2-F | H | CH |
| 5.04 | CH$_3$ | 2-chlorophenyl | 2-F | H | CH |
| 5.05 | C$_2$H$_5$ | CCl$_3$ | 2-Cl | 4-Cl | N |
| 5.06 | CH$_3$ | phenyl | 2-Cl | 4-CF$_3$ | N |
| 5.07 | CH$_3$ | phenyl | 2-Cl | 4-CF$_3$ | N |
| 5.08 | CH$_3$ | 2-fluorophenyl | 2-Cl | H | CH |

TABLE 3

Compounds of the formula IIb$_2$

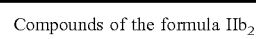

(IIb$_2$)

| Comp. No. | R$_{68}$ | R$_{67}$ | R$_{66}$ | R$_{12}$ | R$_{13}$ |
|---|---|---|---|---|---|
| 6.01 | CH$_3$ | CH$_3$ | CH$_3$ | 2-Cl | 4-Cl |
| 6.02 | CH$_3$ | C$_2$H$_5$ | CH$_3$ | 2-Cl | 4-Cl |
| 6.03 | CH$_3$ | C$_2$H$_5$ | C$_2$H$_5$ | 2-Cl | 4-Cl |

TABLE 4

Compounds of the formula IIc

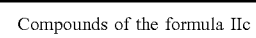

(IIc)

| Comp. No. | A$_2$ | R$_{26}$ |
|---|---|---|
| 7.001 |  OCH$_3$ | H |

TABLE 4-continued

Compounds of the formula IIc

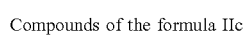

(IIc)

| Comp. No. | A$_2$ | R$_{26}$ |
|---|---|---|
| 7.002 | CH$_3$, CH$_3$ (2,4-dimethylphenyl) | H |
| 7.003 | 1-methylnaphthyl | CH$_3$ |
| 7.004 | 2-methoxyphenyl (OCH$_3$) | CH$_3$ |

TABLE 5

Compounds of the formula IIe

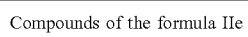

(IIe)

| Comp. No. | R$_{33}$ | R$_{34}$ | R$_{33}$ + R$_{34}$ |
|---|---|---|---|
| 8.001 | CH$_2$=CHCH$_2$ | CH$_2$=CHCH$_2$ | — |
| 8.002 | — | — | 2,2-dimethyltetrahydrofuran |
| 8.003 | CH$_3$ (methyl-dimethyl-tetrahydrofuran) | | — |
| 8.004 | — | CH$_3$ (methyl-dimethyl-tetrahydrofuran) | |

TABLE 5-continued

Compounds of the formula IIe (IIe)

[Structure: R33-N(R34)-C(=O)-CHCl2]

| Comp. No. | R33 | R34 | R33 + R34 |
|---|---|---|---|
| 8.005 | — | | [furan-tetrahydrofuran bicyclic structure with CH3 CH3] |
| 8.006 | — | | [chromane structure with CH3] |
| 8.007 | — | | [indolizidinone structure with CH3 CH3 and CH3] |

TABLE 6

Compounds of the formula IIf (IIf)

[Structure: R63-phenyl-C(R64)=N-O-CH2-dioxolane]

| Comp. Nr. | R63 | R64 |
|---|---|---|
| 9.01 | H | CN |
| 9.02 | Cl | $CF_3$ |

TABLE 7

Compounds of the formula IIg (IIg)

[Structure: R65-phenyl-pyrimidine with two Cl]

| Comp. No. | R65 |
|---|---|
| 10.01 | H |
| 10.02 | $CH_3$ |

The safeners given in Tables 1 to 7 and their preparation are disclosed, for example, in EP-A-492 366, WO 91/7874 and WO 94/987.

Herbicidal compositions according to the invention which are very especially important are those which comprise one of the combinations of active ingredients below:

Ia+4.01; Ia+4.02; Ia+4.03; Ia+4.04; Ib, where R is hydrogen, +4.01; Ib, where R is hydrogen, +4.02; Ib, where R is hydrogen, +4.03; Ib, where R is hydrogen, +4.04; Ib, where R is fluorine, +4.01; Ib, where R is fluorine, +4.02; Ib, where R is fluorine, +4.03; Ib, where R is fluorine, +4.04;

Ia+5.01; Ia+5.02; Ia+5.03; Ia+5.04; Ia+5.05; Ia+5.06; Ia+5.07; Ia+5.08; Ib, where R is hydrogen, +5.01; Ib, where R is hydrogen, +5.02; Ib, where R is hydrogen, +5.03; Ib, where R is hydrogen, +5.04; Ib, where R is hydrogen, +5.05; Ib, where R is hydrogen, +5.06; Ib, where R is hydrogen, +5.07; Ib, where R is hydrogen, +5.08; Ib, where R is fluorine, +5.01; Ib, where R is fluorine +5.02; Ib, where R is fluorine, +5.03; Ib, where R is fluorine, +5.04; Ib, where R is fluorine, +5.05; Ib, where R is fluorine, +5.06; Ib, where R is fluorine, +5.07; Ib, where R is fluorine, +5.08;

Ia+6.03; Ib, where R is hydrogen, +6.03; Ib, where R is fluorine, +6.03; Ia+7.01; Ia+7.02; Ia+7.03; Ia+7.04; Ib, where R is hydrogen, +7.01; Ib, where R is hydrogen, +7.02; Ib, where R is hydrogen, +7.03; Ib, where R is hydrogen, +7.04; Ib, where R is fluorine, +7.01; Ib, where R is fluorine, +7.02; Ib, where R is fluorine, +7.03; and Ib, where R is fluorine, +7.04.

The invention also relates to a method for the selective control of weeds in crops of useful plants which consists in treating the useful plants, their seeds or vegetative propagation material or the area on which they are grown either simultaneously or separately with a herbicidally active amount of the herbicide of the formula Ia and/or Ib and a herbicidally antagonistically active amount of the safener of the formula II.

Suitable crop plants which can be protected by the safeners of the formula II against the damaging action of the abovementioned herbicides are, in particular, cereals and rice. Crops are also to be understood as meaning those which have been made tolerant to herbicides or classes of herbicides by means of conventional breeding or genetic engineering methods.

The weeds to be controlled can be either monocotyledon or dicotyledon weeds, for example *Stellaria, Nasturtium, Agrostis, Digitaria, Avena, Setaria, Sinapis, Lolium, Solanum, Phaseolus, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola* and *Veronica*.

"Areas on which they grow" are the areas of soil on which the crop plants grow already or which are sown with the seed of these crop plants, but also the soils intended to be planted with these crop plants.

Depending on the intended purpose, a safener of the formula II can be employed for pretreating the seed of the crop plant (seed dressing or treatment of propagation material) or incorporated into the soil before or after sowing. However, it can also be applied alone or together with the herbicide once the plants have emerged. Treatment of the plants or of the seed with the safener can therefore be effected in principle independently of the point in time at which the herbicide is applied. However, the plant can also be treated by simultaneously applying herbicide and safener (for example as a tank mix).

The application of safener to be applied relative to the herbicide depends largely on the type of application. In the case of field treatment, where either a combination of safener and herbicide is applied using a tank mix or where safener and herbicide are applied separately, the ratio of herbicide to safener is, as a rule, from 1:100 to 1:1, preferably 1:50 to 5:1.

As a rule, 0.001 to 5.0 kg of safener/ha, preferably 0.001 to 0.5 kg of safener/ha, are applied for field treatment.

As a rule, the rates of application of herbicide are between 0.001 and 2 kg/ha, but preferably between 0.005 to 1 kg/ha.

The compositions according to the invention are suitable for all application methods conventionally used in agriculture, for example pre-emergence application, post-emergence application and seed dressing.

For seed dressing, 0.001 to 10 g of safener/kg of seed, preferably 0.05 to 2 g of safener/kg of seed, are generally applied. If the safener is applied in liquid form shortly before sowing by seed soaking, it is expedient to use safener solutions which comprise the active ingredient at a concentration of from 1 to 10000, preferably from 100 to 1000, ppm.

For application, the safeners of the formula II or combinations of these safeners with the herbicides of the formula Ia and/or Ib and/or Ic are expediently processed together with the auxiliaries conventionally used in the art of formulation to give formulations, for example emulsion concentrates, spreadable pastes, directly sprayable or dilutable solutions, dilute emulsions, wettable powders, soluble powders, dusts, granules or microcapsules. The formulations are prepared in a known manner, for example by intimately mixing and/or grinding the active ingredients with liquid or solid formulation auxiliaries, for example solvents or solid carriers. Furthermore, surface-active compounds (surfactants) can additionally be used in the preparation of the formulations.

The following are suitable as solvents: aromatic hydrocarbons, preferably the fractions $C_8$ to $C_{12}$, for example xylene mixtures or substituted naphthalenes, phthalic esters such as dibutyl phthalate or dioctyl phthalate, aliphatic hydrocarbons such as cyclohexane or paraffins, alcohols and glycols or else their ethers and esters such as ethanol, ethylene glycol, ethylene glycol monomethyl ether or ethylene glycol monoethyl ether, ketones such as cyclohexanone, strongly polar solvents such as N-methyl-2-pyrrolidone, dimethyl sulfoxide or N,N-dimethylformamide, and epoxidized or unepoxidized vegetable oils such as epoxidized coconut oil or soya oil; or water.

Solid carriers which are used for example for dusts and dispersible powders are, as a rule, ground natural minerals such as calcite, talc, kaolin, montmorillonite or attapulgite. To improve the physical properties of the formulations, highly-disperse silicic acid or highly-disperse absorptive polymers may also be added. Suitable particulate, adsorptive carriers for granules are porous types, for example pumice, brick grit, sepiolite or bentonite, and examples of non-sorptive carrier materials are calcite or sand. In addition, a large number of pregranulated materials of inorganic or organic nature can be used such as, in particular, dolomite or comminuted plant residues.

Suitable surface-active compounds are, depending on the nature of the active ingredient of the formula I to be formulated, non-ionic, cationic and/or anionic surfactants and surfactant mixtures which have good emulsifying, dispersing and wetting properties.

Suitable anionic surfactants can be so-called water-soluble soaps, as well as water-soluble synthetic surface-active compounds.

Soaps which may be mentioned are the alkali metal salts, alkaline earth metal salts or substituted or unsubstituted ammonium salts of higher fatty acids ($C_{10}$–$C_{22}$), for example the sodium or potassium salts of oleic or stearic acid, or of natural fatty acid mixtures which can be obtained from, for example, coconut oil or tallow oil. The fatty acid methyltauride salts may also be mentioned.

However, so-called synthetic surfactants, in particular fatty alcohol sulfonates, fatty alcohol sulfates, sulfonated benzimidazol derivatives or alkylaryl sulfonates, are used more frequently.

As a rule, the fatty alcohol sulfonates or fatty alcohol sulfates are present in the form of alkali metal salts, alkaline earth metal salts or substituted or unsubstituted ammonium salts and have an alkyl radical of 8 to 22 C atoms, alkyl also embracing the alkyl moiety of acyl radicals, for example the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated and benzimidazole derivatives have preferably two sulfonic acid groups and a fatty acid radical with approximately 8–22 C atoms. Alkylarylsulfonates are, for example, the sodium salts, calcium salts or triethanolamine salts of dodecylbenzenesulfonic acid, of dibutylnaphthalene sulfonic acid or of a naphthalenesulfonic acid/formaldehyde condensate.

Suitable phosphates, for example salts of the phosphoric ester of a p-nonylphenol/(4–14)-ethyleneoxide adduct, or phospholipids, are furthermore also suitable.

Suitable non-ionic surfactants are mainly polyglycol ether derivatives of aliphatic or cycloaliphatic alcohols, saturated or unsaturated fatty acids and alkylphenols, and these derivatives can have 3 to 30 glycol ether groups and 8 to 20 carbon atoms in the (aliphatic) hydrocarbon radical and 6 to 18 carbon atoms in the alkyl radical of the alkylphenol.

Other suitable non-ionic surfactants are the water-soluble adducts of polyethylene oxide to polypropylene glycol, ethylene diaminopolypropylene glycol and alkyl polypropylene glycol which have 1 to 10 carbon atoms in the alkyl chain and 20 to 250 ethylene glycol ether groups and 10 to 100 propylene glycol ether groups. The compounds mentioned normally have 1 to 5 ethylene glycol units per propylene glycol unit.

Examples of non-ionic surfactants which may be mentioned are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Other substances which are suitable are fatty acid esters of polyoxyethylene sorbitan, such as polyoxyethylene sorbitan trioleate.

The cationic surfactants are mainly quaternary ammonium salts which have, as N substituents, at least one alkyl radical of 8 to 22 C atoms and, as further substituents, lower, halogenated or unhalogenated alkyl, benzyl or lower hydroxyalkyl radicals. The salts are preferably in the form of halides, methylsulfates or ethylsulfates. Examples are stearyl trimethylammonium chloride and benzyl di(2-chloroethyl)ethyl ammonium bromide.

The surfactants conventionally used in the art of formulation which can also be used in the compositions according to the invention are described, inter alia, in "Mc Cutcheon's Detergents and Emulsifiers Annual" MC Publishing Corp., Ridgewood N.J., 1981, Stache, H., "Tensid-Taschenbuch" [Surfactants Guide], Carl Hanser Verlag, Munich/Vienna, 1981, and M. and J. Ash, "Encyclopedia of Surfactants", Vol I–III, Chemical Publishing Co., New York, 1980–81.

As a rule, the herbicidal formulations comprise 0.1 to 99% by weight, in particular 0.1 to 95% by weight, of active ingredient mixture of the compound of the formula Ia and/or Ib and/or Ic with the compounds of the formulae II, 1 to 99.9% by weight of a solid or liquid formulation auxiliary and 0 to 25% by weight, in particular 0.1 to 25% by weight, of a surfactant.

While concentrated compositions are normally preferred as commercially available goods, the consumer uses, as a rule, dilute compositions.

The compositions can also comprise other additives such as stabilizers, for example epoxidized or unepoxidized vegetable oils (epoxidized coconut oil, rapeseed oil or soya oil), antifoams, for example silicone oil, preservatives, viscosity regulators, binders, tackifiers and fertilizers or other active ingredients.

A variety of methods and techniques, for example those given below, are suitable for the use of safeners of the formula II or of compositions comprising them for protecting crop plants against damaging effects of herbicides of the formula Ia and/or Ib and/or Ic:

i) Seed Dressing a) Dressing of the seeds with an active ingredient of the formula II, formulated as a wettable powder, by shaking in a container until the active ingredient is distributed uniformly on the seed surface (dry seed treatment). Approximately 1 to 500 g of active ingredient of the formula II (4 g to 2 kg of wettable powder) are used per 100 kg of seed.

b) Dressing of the seeds with an emulsion concentrate of the active ingredient of the formula II following method a) (wet seed treatment).

c) Seed dressing by immersing the seed in a mixture comprising 100–1000 ppm of active ingredient of the formula II for 1 to 72 hours, if desired followed by drying the seeds (immersion treatment).

Naturally, seed dressing or treatment of the seed kernel which has begun to germinate are the preferred application methods because the treatment with active ingredient is directed entirely at the target crop. As a rule, 1 to 1000 g of antidote, preferably 5 to 250 g of antidote, are used per 100 kg of seed, it being possible to deviate beneath or beyond the limit concentrations given, depending on the methodology, which also allows the addition of other active ingredients or micronutrients (repeated treatment).

ii) Application as a Tank Mix

A liquid formulation of a mixture of antidote and herbicide (mutual weight ratio between 10:1 and 1:100) is used, the rate of application of herbicide being 0.005 to 5.0 kg per hectare. Such tank mixes are applied before or after sowing.

iii) Application into the Seed Furrow

The safener is introduced into the open, seeded seed furrow in the form of an emulsion concentrate, wettable powder or granules. After the seed furrow has been covered, the herbicide is applied pre-emergence in the customary manner.

iv) Controlled Release of Active Ingredient

The active ingredient of the formula II is applied, as a solution, to mineral carriers for granules or to polymerized granules (urea/formaldehyde) and dried. If desired, a coating may be applied (coated granules) which allows the active ingredient to be released over a given period at a particular dosage rate.

Preferred formulations have the following compositions in particular:

(%=percent by weight)

Dusts:

| | |
|---|---|
| Active ingredient mixture: | 0.1 to 10%, preferably 0.1 to 5% |
| solid carrier: | 99.9 to 90%, preferably 99.9 to 99% |

-continued

Suspension concentrates:

| | |
|---|---|
| Active ingredient mixture: | 5 to 75%, preferably 10 to 50% |
| Water: | 94 to 24%, preferably 88 to 30% |
| Surfactant: | 1 to 40%, preferably 2 to 30% |

Wettable powders:

| | |
|---|---|
| Active ingredient mixture: | 0.5 to 90%, preferably 1 to 80% |
| Surfactant: | 0.5 to 20%, preferably 1 to 15% |
| Solid carrier material: | 5 to 95%, preferably 15 to 90% |

Granules:

| | |
|---|---|
| Active ingredient mixture: | 0.1 to 30%, preferably 0.1 to 15% |
| Solid carrier: | 99.5 to 70%, preferably 97 to 85% |

The examples which follow illustrate the invention in greater detail without imposing any limitation.

Formulation Examples for Mixtures of Herbicides of the Formula I and/or Ib and/or Ic and safeners of the formula II (%=percent by weight)

| F1. Solutions | | | | |
|---|---|---|---|---|
| | a) | b) | c) | d) |
| Active ingredient mixture | 5% | 10% | 50% | 90% |
| 1-Methoxy-3-(3-methoxy-propoxy)propane | — | 20% | 20% | — |
| Polyethylene glycol MW 400 | 20% | 10% | — | — |
| N-Methyl-2-pyrrolidone | — | — | 30% | 10% |
| Aromatic hydrocarbon mixture $C_9$–$C_{12}$ | 75% | 60% | — | — |

The solutions are suitable for use in the form of microdrops.

| F2. Wettable powders | | | | |
|---|---|---|---|---|
| | a) | b) | c) | d) |
| Active ingredient mixture | 5% | 25% | 50% | 80% |
| Sodium lignosulfonate | 4% | — | 3% | — |
| Sodium lauryl sulfate | 2% | 3% | — | 4% |
| Sodium diisobutylnaphthylene-sulfonate | — | 6% | 5% | 6% |
| Octylphenyl polyglycol ether (7–8 mol of EO) | — | 1% | 2% | — |
| Highly disperse silica | 1% | 3% | 5% | 10% |
| Kaolin | 88% | 62% | 35% | — |

The active ingredient is mixed thoroughly with the additives and the mixture is ground thoroughly in a suitable mill. This gives wettable powders which can be diluted with water to give suspensions of any desired concentration.

| F3. Coated granules | | | |
|---|---|---|---|
| | a) | b) | c) |
| Active ingredient mixture | 0.1% | 5% | 15% |
| Highly disperse silica | 0.9% | 2% | 2% |
| Inorganic carrier material (Ø 0.1–1 mm), for example $CaCO_3$ or $SiO_2$ | 99.0% | 93% | 83% |

The active ingredient is dissolved in methylene chloride, the solution is sprayed onto the carrier, and the solvent is subsequently evaporated in vacuo.

F4. Coated granules

|  | a) | b) | c) |
|---|---|---|---|
| Active ingredient mixture | 0.1% | 5% | 15% |
| Polyethylene glycol MW 200 | 1.0% | 2% | 3% |
| Highly disperse silica | 0.9% | 1% | 2% |
| Inorganic carrier material (Ø 0.1–1 mm), for example CaCO$_3$ or SiO$_2$ | 98.0% | 92% | 80% |

In a mixer, the finely ground active ingredient is applied uniformly to the carrier material which has been moistened with polyethylene glycol. This gives dust-free coated granules.

F5. Extruder granules

|  | a) | b) | c) | d) |
|---|---|---|---|---|
| Active ingredient mixture | 0.1% | 3% | 5% | 15% |
| Sodium lignosulfonate | 1.5% | 2% | 3% | 4% |
| Carboxymethylcellulose | 1.4% | 2% | 2% | 2% |
| Kaolin | 97.0% | 93% | 90% | 79% |

The active ingredient is mixed with the additives, and the mixture is ground and moistened with water. This mixture is extruded and subsequently dried in a stream of air.

F6. Dusts

|  | a) | b) | c) |
|---|---|---|---|
| Active ingredient mixture | 0.1% | 1% | 5% |
| Talc | 39.9% | 49% | 35% |
| Kaolin | 60.0% | 50% | 60% |

Ready-to-use dusts are obtained by mixing the active ingredient with the carriers and grinding the mixture in a suitable mill.

F7. Suspension concentrates

|  | a) | b) | c) | d) |
|---|---|---|---|---|
| Active ingredient mixture | 3% | 10% | 25% | 50% |
| Ethylene glycol | 5% | 5% | 5% | 5% |
| Nonylphenyl polyglycol ether (15 mol of EO) | — | 1% | 2% | — |
| Sodium lignosulfonate | 3% | 3% | 4% | 5% |
| Carboxymethylcellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active ingredient is mixed intimately with the additives. This gives a suspension concentrate from which suspensions of any desired concentration can be prepared by dilution with water.

Frequently, it is more convenient to formulate the active ingredient of the formula I and/or Ib and/or Ic and the other component of the formula II singly and to combine them in water briefly before application in the applicator in the desired mixing ratio as a "tank mix".

The ability of the safeners of the formula II to protect crop plants against the phytotoxic effect of herbicides of the formula Ia and/or Ib and/or Ic is illustrated in the examples which follow.

BIOLOGICAL EXAMPLES

Example B1

Post-Emergence Applications of Mixtures of a Herbicide of the Formula Ia and/or Ib and/or Ic with a Safener of the Formulae IIa to IIg to Cereals Wheat is grown in plastic pots under greenhouse conditions until it has reached the 2.5-leaf stage. At this stage, both the herbicides of the formula Ia and/or Ib and/or Ic alone and the mixture of the herbicides with a safener of the formulae IIa to IIg are applied to the test plants. Application is effected in the form of an aqueous suspension of the test substances (Formulation Example F7) with 500 l of water/ha. 28 days after application, the test is evaluated using a percentage scale. The results obtained demonstrate that the damage to wheat caused by the herbicide of the formula Ia and/or Ib and/or Ic can be reduced markedly by using the safeners of the formulae IIa to IIg.

The same results are obtained when compounds of the formula Ia and/or Ib are formulated as shown in Examples F1 to F6.

What is claimed is:

1. A selectively herbicidal composition which comprises, besides customary inert formulation auxiliaries, as active ingredient a mixture of
    a) a herbicidally active amount of a herbicide selected from the group consisting of the compounds of the formula Ia

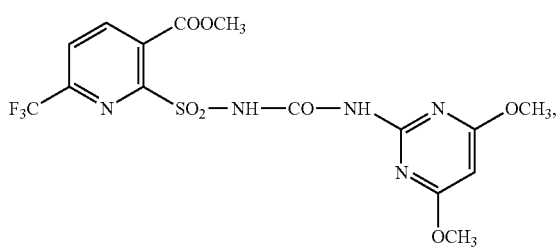

(Ia)

and/or Ib

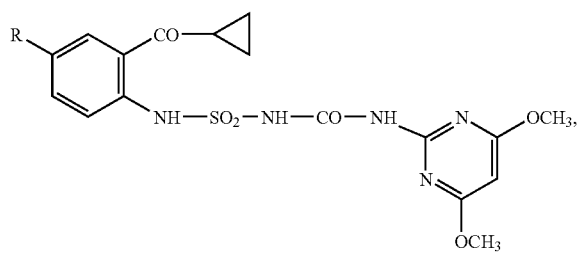

(Ib)

in which R is hydrogen or fluorine and/or Ic

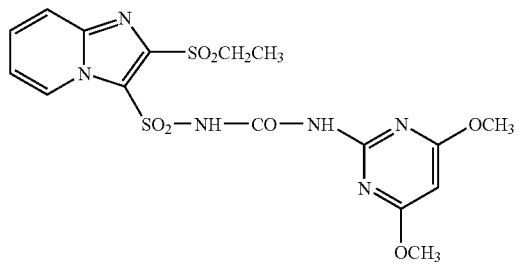

(Ic)

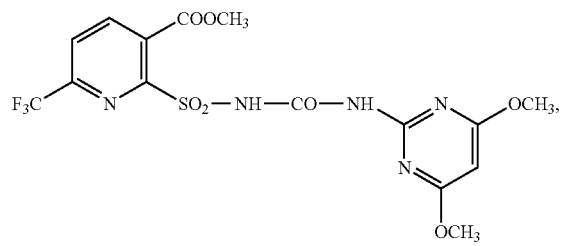

(Ia)

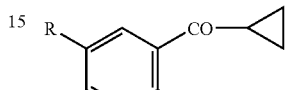

(Ib)

or of a salt of the compounds of the formulae Ia and/or Ib and/or Ic and b) a herbicidally antagonistically active amount of a compound of the formula IIa

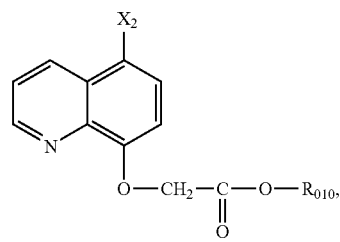

(IIa)

in which $R_{010}$ is —$CH(CH_3)C_5H_{11}$-n; and $X_2$ is chlorine.

2. A composition according to claim 1, which comprises, as compound of the formula Ia, the compound of the formula Id

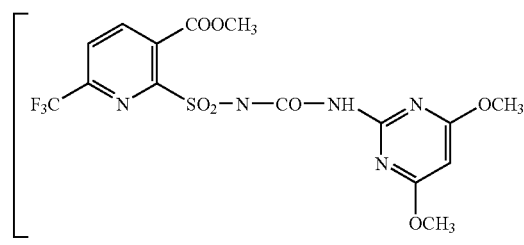

(Id)

3. A composition according to claim 1, which comprises, as herbicide, either the compound of the formula Ia or Id and, as safener, the compound of the formula IIa in which $X_2$ is chlorine and $R_{010}$ is 1-methylhexyl.

4. A composition according to claim 1, which comprises a herbicidally active amount of a herbicide selected from the group consisting of the compounds of the formulae Ia and/or Ib in which R is hydrogen or fluorine, or of a salt of the compounds of the formulae Ia and/or Ib.

5. A herbicide/safener composition according to claim 1, wherein the composition comprises 0.1 to 99% by weight of active ingredient mixture of the compound of the formula Ia and/or Ib and/or Ic with a compound of the formula IIa and 1 to 99.9% by weight of a solid or liquid formulation auxiliary.

6. A herbicide/safener composition according to claim 1, wherein the composition comprises the active compounds Ia and/or Ib and/or Ic and IIa in a weight ratio of from 1:100 to 1:1.

7. A method for the selective control of weeds and grasses in crops of useful plants, which comprises treating the useful plants, their seeds or vegetative propagation material or the area on which they are grown either simultaneously or separately with a herbicidally active amount of a herbicide of the formula Ia and/or Ib and/or Ic according to claim 1 and a herbicidally-antagonistically active amount of a safener of the formula IIa according to claim 1.

8. A method according to claim 7, wherein crops of useful plants or areas on which the crops of useful plants are grown are treated with 0.001 to 2 kg/ha of a herbicide of the formula Ia and/or Ib and/or Ic and an amount of 0.001 to 0.5 kg/ha of a safener of the formula IIa.

9. A method according to claim 7, wherein the crops of useful plants are cereals or rice.

10. A herbicide/safener composition, which comprises a) a herbicidally active amount of a herbicide of the formula Ia

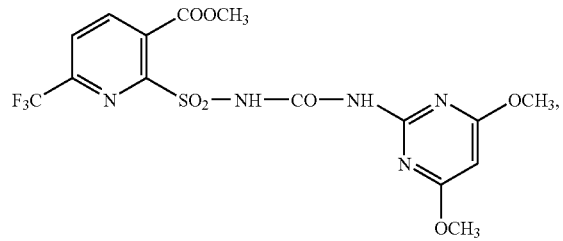

(Ia)

and b) a herbicidally antagonistically active amount of a compound of the formula IIa

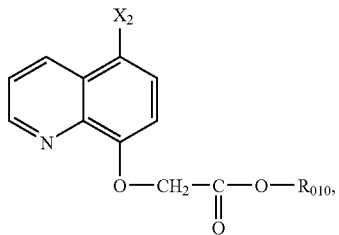

(IIa)

in which $R_{010}$ is —CH(CH$_3$)C$_5$H$_{11}$-n; and $X_2$ is chlorine.

11. A herbicide/safener composition according to claim 10, wherein the composition comprises 0.1 to 99% by weight of active ingredient mixture of the compound of the formula Ia with a compound of the formula IIa and 1 to 99.9% by weight of a solid or liquid formulation auxiliary.

12. A herbicide/safener composition according to claim 10, wherein the composition comprises the active compounds Ia and IIa in a weight ratio of from 1:100 to 1:1.

13. A method for the selective control of weeds and grasses in crops of useful plants, which comprises treating the useful plants, their seeds or vegetative propagation material or the area on which they are grown either simultaneously or separately with a herbicidally active amount of a herbicide of the formula Ia according to claim 10 and a herbicidally-antagonistically active amount of a safener of the formula IIa according to claim 10.

* * * * *